(12) United States Patent
Diederich

(10) Patent No.: US 6,599,013 B1
(45) Date of Patent: Jul. 29, 2003

(54) INTRAORAL DENTAL RADIOLOGY POSITIONING DEVICE

(76) Inventor: Jennifer A. Diederich, 1730 B Farmington Ave., Unionville, CT (US) 06085

( * ) Notice: Subject to any disclaimer, the term of this patent is extended or adjusted under 35 U.S.C. 154(b) by 0 days.

(21) Appl. No.: 10/113,401

(22) Filed: Apr. 1, 2002

(51) Int. Cl.[7] ............................................. G03B 42/02
(52) U.S. Cl. ...................................... 378/170; 378/191
(58) Field of Search .............................. 378/168–170, 378/191

(56) References Cited

U.S. PATENT DOCUMENTS

| | | |
|---|---|---|
| RE25,773 E | 5/1965 | Medwedeff |
| 3,304,422 A | 2/1967 | Medwedeff |
| 3,745,344 A | 7/1973 | Updegrave |
| 4,507,798 A | 3/1985 | Welander |
| D281,353 S | 11/1985 | Sico, Jr. |
| 4,554,676 A | 11/1985 | Maldonado et al. |
| D283,157 S | 3/1986 | Maldonado et al. |
| 5,090,047 A | 2/1992 | Angotti et al. |

OTHER PUBLICATIONS

Goaz & White, Health Physics. *Radiation Safety and Protection*, pp. 53–68. (prior to 2000).
Margraf Corp. Film Positioning Instruments. pp. 1–3. (http://www.margrafcorp.com/FPI.htm) (2002).
Margraf Corp. Rectangular Positioning Indicating Devices. pp. 1–12 (http://www.margrafcorp.com/RectPID.htm) (2002).
PracticonDental Catalog. *Fully Redesigned Rinn XCP Film Holders Improve Patient Comfort, Staff Efficiency.* pp. 57 and 58. (prior to 2002).
Mackie X–ray Advertisment. *RAPD Intra Oral System.* (prior to 2002).
Dentsply Rinn Catalog. *Film Holding Instruments.* pp. 15, 16, 17 and 27. (1997).
Masel Catalog. *Masel Precision X–Ray Film Holders.* pp. 9–13. (1995).

*Primary Examiner*—Craig E. Church
(74) *Attorney, Agent, or Firm*—DeLio & Peterson, LLC; Peter W. Peterson

(57) ABSTRACT

A receptor positioning device for taking dental bitewing radiographs of teeth inside a patient's mouth includes a rigid, fixed structure having a collimation plate defining a substantially rectangular opening. A receptor holding member is adapted to receive a receptor, and an elongated arm is adapted to receive and couple to the collimation plate. The elongated arm extends towards and couples with a rear portion of the receptor holding member, opposite the collimation plate, such that an unobstructed path is defined between the substantially rectangular opening of the collimation plate and the receptor. A biting surface is fixedly attached to a distal end of the elongated arm and adjacent to the receptor holding member such that the receptor is positioned behind the teeth on which the radiographs are being taken while the biting surface is gripped by the teeth on the opposite side of the patient's mouth.

12 Claims, 11 Drawing Sheets

INTRAORAL DENTAL RADIOLOGY POSITIONING DEVICE

BACKGROUND OF THE INVENTION

1. Field of the Invention

The present invention relates to devices for dental radiographic procedures or intraoral diagnostics, and more particularly, to intraoral dental radiology positioning devices relating to positioning x-ray film or receptors in a patient's mouth during radiographic procedures.

2. Description of Related Art

Intraoral x-ray diagnosis involves positioning an x-ray film within a patient's mouth next to the inner surface of the teeth or bone being studied. The film is then exposed to an x-ray beam generated outside the mouth and passing through the target. Known intraoral dental radiography typically employs a dental device having an alignment member including an x-ray film holding structure at one end, an aligning arm at another end, and a bite plate positioned between the ends. The alignment member may include a collimation structure for collimation of an x-ray beam to conform more accurately to the size and shape of the x-ray film held by the film holding structure. A commonly prescribed dental radiograph is the "bitewing", whereby an image is acquired of the crowns of the teeth biting together and their surrounding socket bone. Also typical is film mounted in a holder which includes a bite block portion extending from the film in the direction of the external x-ray tube. The patient bites down on the bite block with the target teeth and holds the film in position next to the target.

Most dental radiographic techniques utilize beams of circular cross-section despite the fact that the dental films are typically rectangular in shape. A disadvantage of known devices is that the cross-sectional area of the beam used by the radiographic technique is typically larger than the surface area of the x-ray film. When the cross-sectional area of the beam does not match the film size, the patient can be exposed to unnecessary radiation which irradiates tissues beyond the borders of the dental film.

Another disadvantage of current x-ray film positioning instruments is that there can be errors in aiming the x-ray. These errors are frequently associated with a rectangular position-indicating device attached to an x-ray machine. Aiming error exposes the patient to needless retakes of radiographs. Common film positioning instruments may also allow unwanted x-radiation to pass through the receptor, or film holding element.

Typical film positioning devices and instruments include multiple parts, requiring assembly and adjustment. The multiple arrangements of parts may lose their set position which can cause a reduction in the sharpness of the acquired image.

Enhancing the ability to sterilize dental equipment is desirable in the field. Current film positioning devices may have disadvantages when sterilizing because parts, such as cushioned areas, may be less accessible or receptive to steam, heat or chemical methods.

Commonly, patients may assist in positioning and holding a film positioning device in their mouth. Typical devices may be difficult to grasp and manipulate in the patient's mouth making it problematic for the patient to assist in positioning the instrument.

Bearing in mind the problems and deficiencies of the prior art, it is therefore an object of the present invention to provide a device which will reduce patient exposure of x-radiation.

It is a further object of the present invention to provide a device which will reduce aiming error and cone cuts.

It is another object of the invention to provide a device which will improve the quality of the acquired image on the receptor-x-ray film.

It is yet another object of the present invention to provide a device which will universally adapt to traditional film and electronic/digital receptors.

It is a further object of the present invention to provide a device which will minimize movement of the interconnected parts of the device once the parts are desirably positioned.

It is another object of the present invention to provide a device which minimizes movement of the device in the patient's mouth.

It is yet another object of the present invention to provide a device which fixedly sets the x-ray source to align with the receptor, or film.

It is a further object of the present invention to provide a device which limits magnification and keeps magnification uniform.

It is another object of the present invention to provide a device which maximizes sharpness of the acquired image on the film.

It is yet another object of the present invention to provide a device which facilitates sterilization.

It is a further object of the present invention to provide a device which facilitates sterilization.

It is another object of the present invention to provide a device which is of maximum durability.

It is yet another object of the present invention to provide a device which minimizes patient discomfort and malpositioning.

It is a further object of the present invention to provide a device which minimizes "retakes" of radiographs.

It is another object of the present invention to provide a method of positioning a film-positioning device in a patient's mouth providing an unobstructed line between an x-ray device and x-ray film.

Still other objects and advantages of the invention will in part be obvious and will in part be apparent from the specification.

SUMMARY OF THE INVENTION

The above and other objects, which will be apparent to those skilled in art, are achieved in the present invention which is directed to, in a first aspect, a receptor positioning device for taking dental bitewing radiographs of a patient's teeth comprising a collimation plate defining a substantially central opening. A receptor holding member is adapted to receive a receptor, and an elongated arm including a biting surface is positioned toward a distal end thereof. The elongated arm is adapted to receive and couple at a first end to the collimation plate. The elongated arm is designed and adapted to extend towards and couple to a rear portion of the receptor holding member, opposite the collimation plate, such that an unobstructed path is defined between the substantially central opening of the collimation plate and the receptor received by the receptor holding member. The receptor holding member may preferably accommodate a plurality of receptor dimensions, films, and digital receptors. In a preferred embodiment of the present invention, the collimation plate, the receptor holding member, and the elongated arm are rigidly fixed together. In another preferred embodiment of the present invention, the collimation plate, the receptor back plate, and the elongated arm are constructed of metal.

In a related aspect, the receptor back plate includes an incompressible receiving portion adapted for biting with the patient's teeth.

In another related aspect, the collimation plate includes handles opposite of one another for the patient to grasp.

In yet another related aspect, the opening in the collimation plate is substantially rectangular in shape and is orientated similarly to the film having a substantially rectangular shape.

In a related aspect, the substantially central opening defined by the collimation plate is adapted to correspond dimensionally to the dimensions of the receptor.

In another related aspect, the biting surface is adjacent to the receptor holding member such that the receptor is positioned behind the patient's teeth.

In another aspect of the present invention, a receptor positioning device for taking dental bitewing radiographs of teeth inside a patient's mouth, comprises a rigid, fixed structure including a collimation plate defining a substantially rectangular opening, a receptor holding member adapted to receive a receptor, and an elongated arm being adapted to receive and couple at a first end to the collimation plate. The elongated arm is designed and adapted to extend towards and couple at a second end to a rear portion of the receptor holding member, opposite the collimation plate, such that an unobstructed path is defined between the substantially rectangular opening of the collimation plate and the receptor received by the receptor holding member. A biting surface is fixedly attached to a distal end of the elongated arm and adjacent to the receptor holding member such that the receptor is positioned behind the teeth on which the radiographs being taken while the biting surface is gripped by teeth on the opposite side of the patient's mouth.

In yet another aspect of the present invention, a method for taking dental bitewing radiographs of a patients' teeth comprises providing a rigid fixed structure including a collimation plate defining a substantially central opening, a receptor holding member adapted to receive a receptor, and an elongated arm being adapted to receive and couple at a first end to the collimation plate. The elongated arm is designed and adapted to extend towards and couple to a rear portion of the receptor holding member such that an unobstructed path is defined between the substantially rectangular opening of the collimation plate and the receptor received by the receptor holding member. A biting surface is provided which is fixedly attached to a distal end of the elongated arm and adjacent to the receptor holding member such that the receptor is positioned behind the patient's teeth on which the radiographs is being taken while the biting surface is gripped by teeth on the opposite side of the patient's mouth. The patient's teeth bite on the biting surface such that an unobstructed path is defined between the collimation plate and the receptor received by the receptor holding member. An x-ray machine is aligned with the opening of the collimation plate, and the receptor is exposed such that x-radiation from the x-ray machine passes along the unobstructed path defined between the collimation plate and the receptor.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
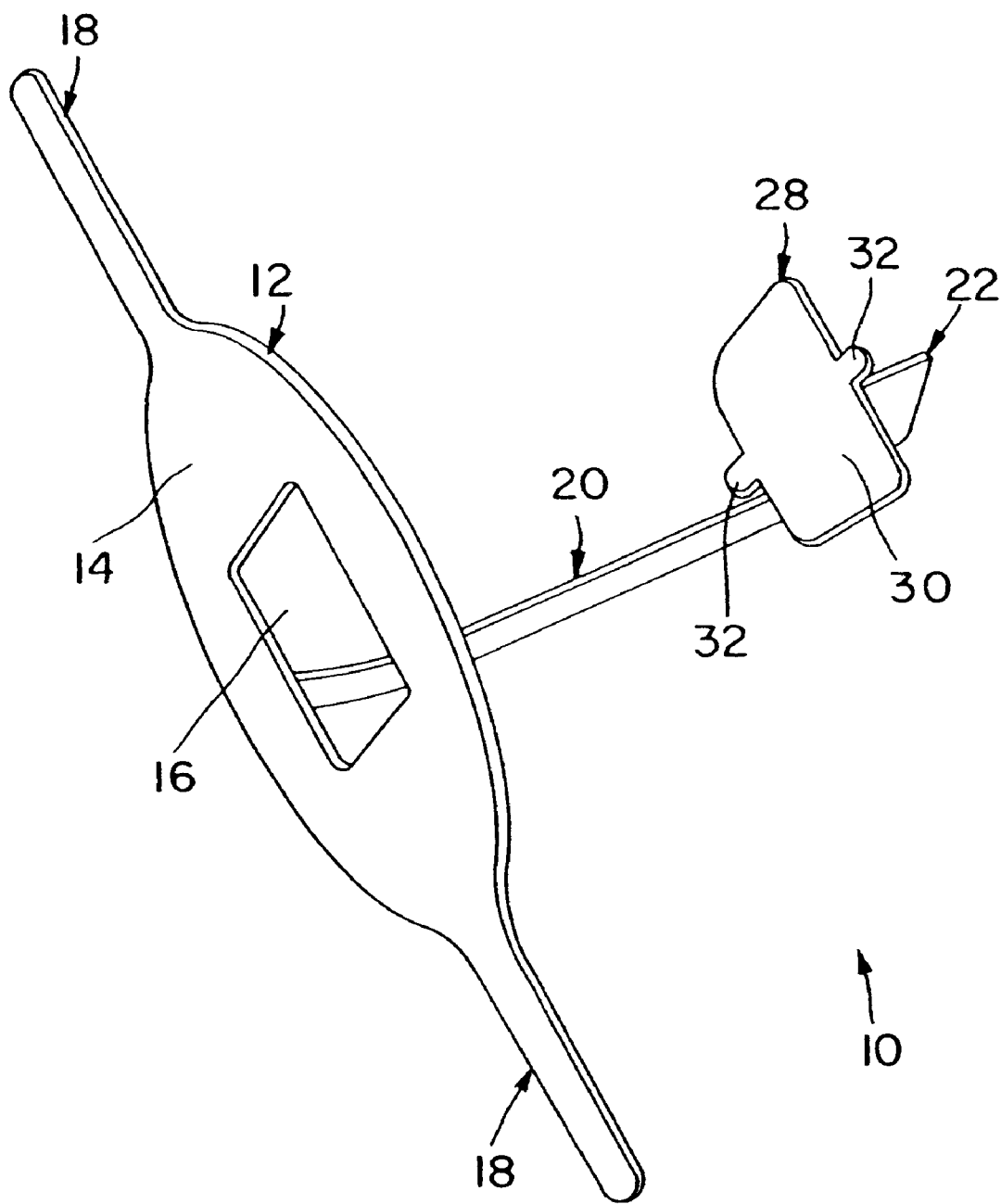
FIG. 1 is a perspective view of the receptor positioning device of the present invention.

In describing the preferred embodiment of the present invention, reference will be made herein to FIGS. 1–15 of the drawings in which like numerals refer to like features of the invention. Features of the invention are not necessarily shown to scale in the drawings.

A preferred embodiment 10 shown in FIGS. 1–6, depicts the intraoral dental radiology receptor positioning device of the present invention. Referring to FIGS. 1–4, the receptor positioning device includes a substantially flat collimation plate 12, having a surface area 14. The surface area 14 defines a substantially central rectangular opening 16. The collimation plate 12 further includes opposing elongated handles 18 extending outward on opposite sides thereof. The receptor positioning instrument 10 further includes an elongated arm 20 and a film or electronic receptor holding member 28 having a back plate 30 and clips 32 for holding x ray film or electronic receptors. The elongated arm 20 is connected at a bent first end 40 to the back of the collimation plate 50, preferably, by welding or other rigid connection. The elongated arm further includes a second end 22 attached to the rear surface 52 of the back plate 30 of the receptor holding member 28, opposite collimator plate 12.

Figure 3:
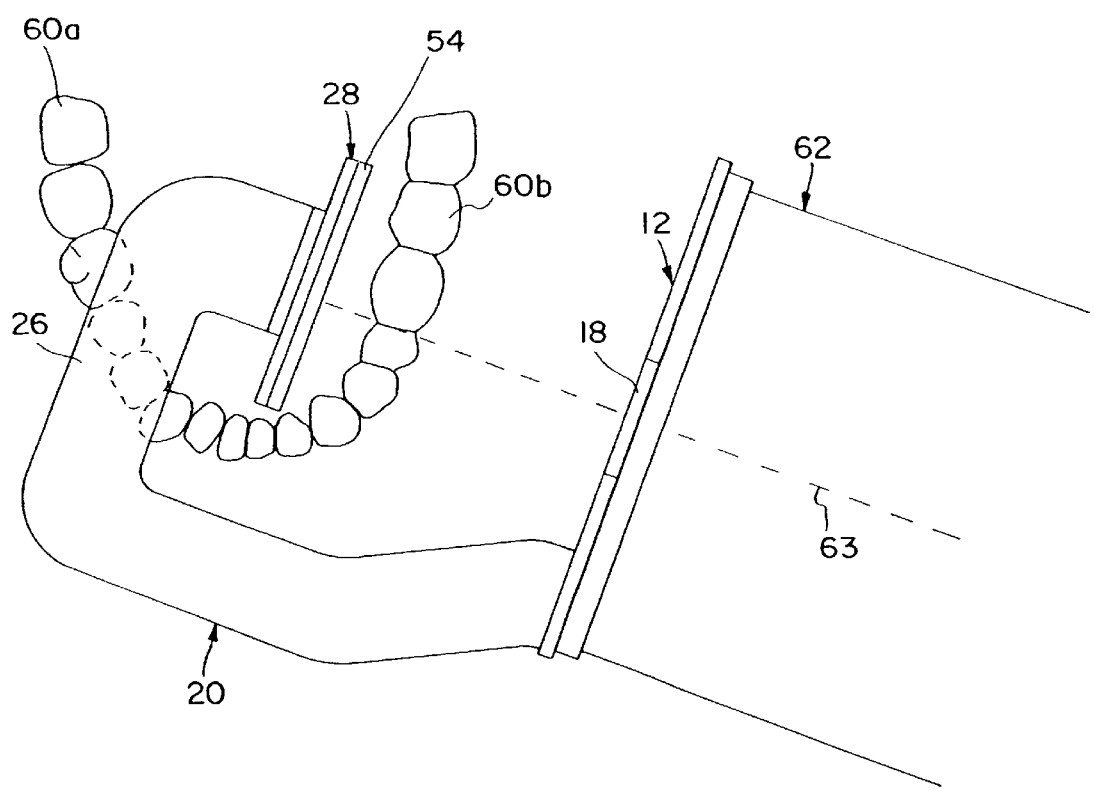
FIG. 3 is a side elevational view of the receptor positioning device shown in FIG. 1 depicting the position of the patient's teeth.
Figure 4:
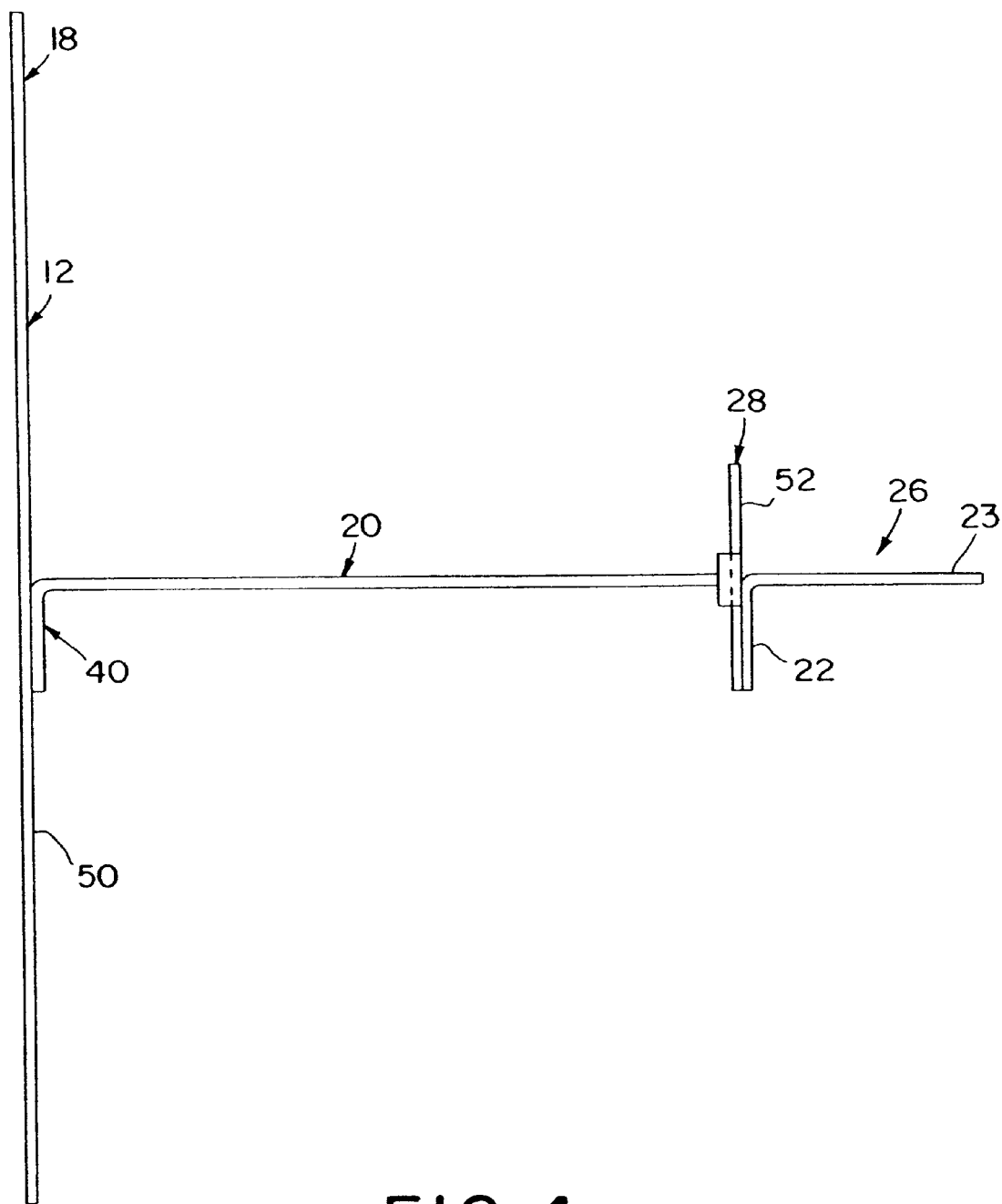
FIG. 4 is another side view of the receptor positioning device shown in FIG. 1 rotated 180° from the view in FIG. 3.

The film or electronic receptor holding member 28. back plate 30 is preferably of metal and the opposing clips 32 are designed and adapted to receive and grasp a removable film or electronic receptor 54. The elongated arm 20 includes a flat upper surface 26 adapted to receive a patient's teeth. The patient's teeth 60a on one side of the mouth are positioned to grip the substantially flat biting surface 26 of the elongated arm 20, as shown in FIG. 3. The film or receptor 54 held on the back plate 30 by the clips 32 of the receptor holding member 28 is positioned behind the desired teeth 60b on the opposite side of the patient's mouth. Preferably, the back plate 30 and receptor 54 are parallel to collimation plate 12. The film or receptor 54 is thereby positioned to be exposed to an x-ray from the x-ray machine 62 to show the condition of teeth 60b, as shown further in FIG. 11.

Figure 2:
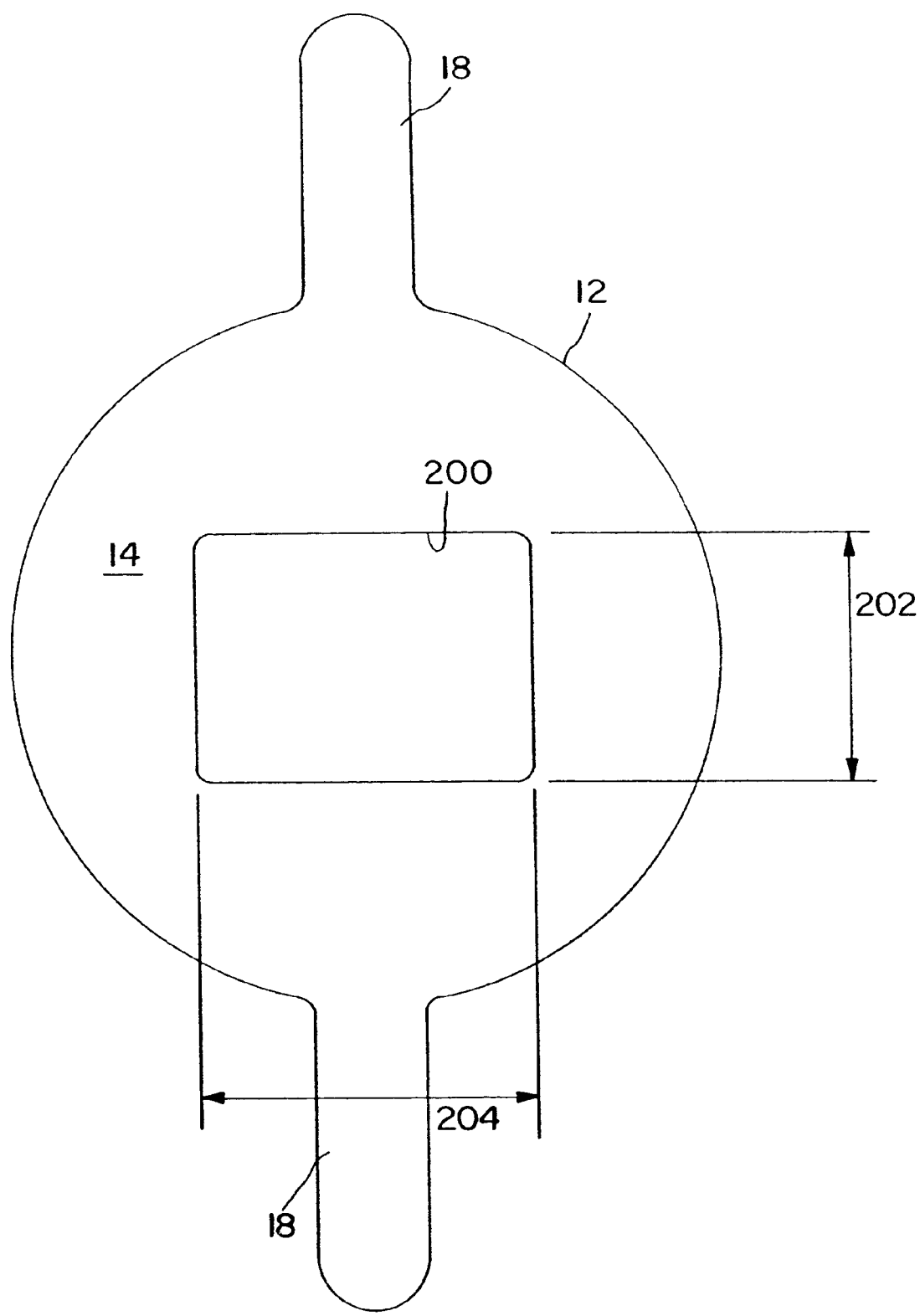
FIG. 2 is a front elevational view of the collimation plate of the device shown in FIG. 1.

Referring to FIG. 2, the collimation plate 12 further includes a preferably rectangular opening 200 positioned substantially in the center of the collimation plate 12. The opening 16 has a vertical dimension 202, and a horizontal dimension 204. In the preferred embodiment shown in FIGS. 1 and 2, the vertical dimension 202 of the opening is about 1.210 inches, and the horizontal dimension 204 is preferably about 1.552 inches. The collimation plate 12 is adapted to axially align the x-ray machine's position indicating cylinder device 62 with the receptor 54, as shown by the x-ray centerline 63. It does this in two ways. First, the x-ray machine is easily centered because the two devices, 12, 62, have substantially the same diameter. Axial offset would be apparent by extension of the outer edge of collimation plate 12 beyond the outer rim of the x-ray machine position indicating cylinder device 62. Second, substantially full, flat contact of the collimation plate 12 with the x-ray machine's position indicating cylinder device 62, as shown in FIG. 3, would assure optimal alignment of the x-ray receptor with the x-ray beam.

The orientation and size of the rectangular collimation opening described above is for use with the adult size horizontal bitewing radiographic examination of patients with normal anatomy and dentitions. Other sizes may be made for small children or for other uses.

Figure 5:
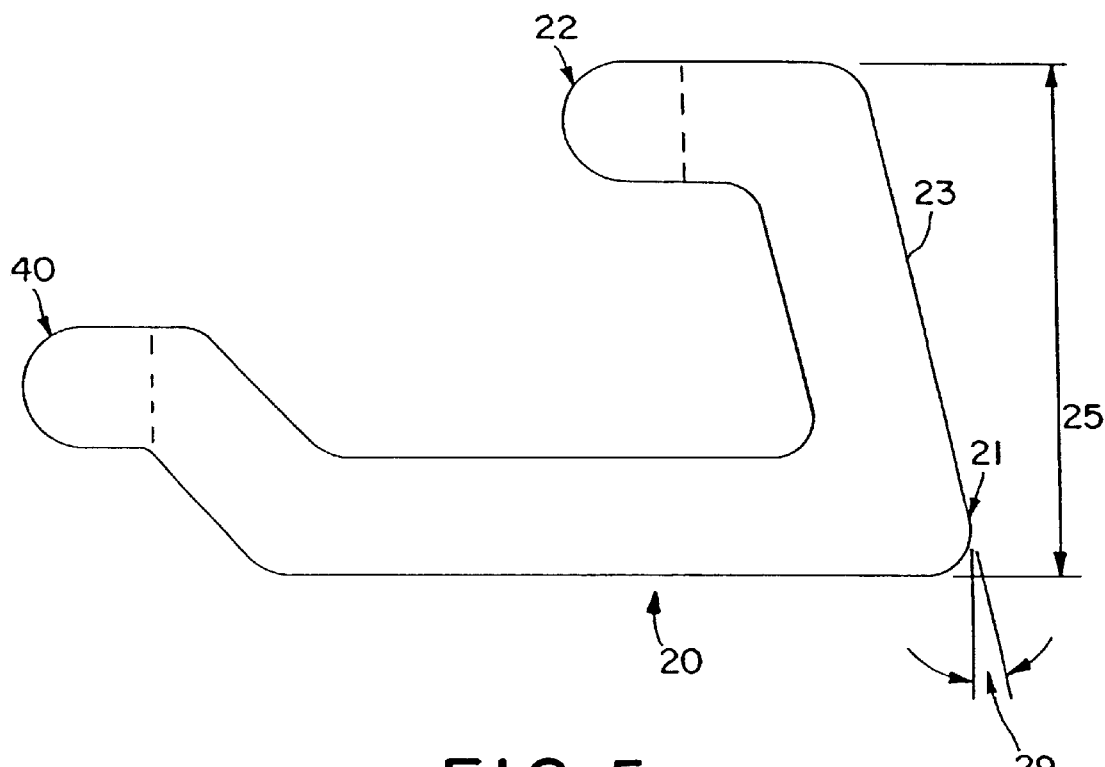
FIG. 5 is a side elevational view of the elongated arm of the receptor positioning device shown in FIG. 1.
Figure 6:
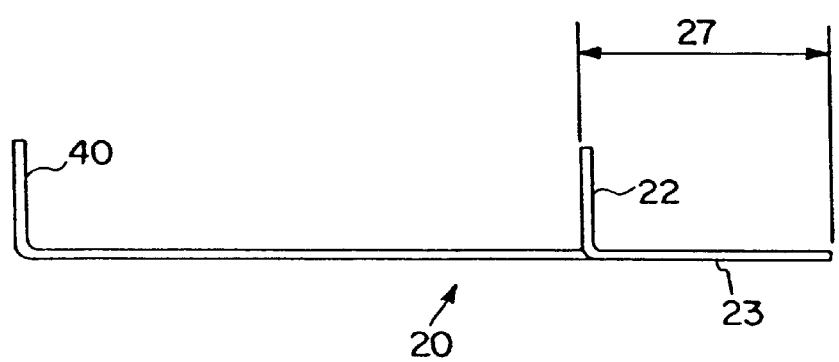
FIG. 6 is a side view of the elongated arm of FIG. 5.

Referring to FIGS. 5 and 6, the substantially flat elongated arm 20 of the preferred embodiment shown in FIG. 1 is shown including the first end 40, the second end 22, a short member 23 (on which biting surface 26 is located) having a first length 25, and an angled portion 21. FIG. 5 shows arm 20 as a flat blank prior to forming at the dotted lines, while FIG. 6 shows arm 20 after forming, where both ends 22 and 40 are bent approximately 90°. The second end 22 of the elongated arm 20, and the outer edge of the angled portion 21 define a first dimension 27. The first dimension 27 is preferably about 1.25 inches, and the first length 25 is preferably about 2.54 inches. The outer edge of the short member 23 and the vertical plane define an angle 29 which determines the angulation of the short member 23 of the elongated arm 20. The preferred angle 29 is about 12°. These dimensions and angles are preferred for three reasons. First, the dimension of the elongated arm is consistent with optimal placement of an x-ray receptor in mouths with normal anatomy and dentitions ranging in size from that of a child (8 years and up) to very large. Second, the dimension of the elongated arm is compatible with accommodating conventional film and digital-electronic receptors currently available. Third, the dimension of the elongated arm is compatible with accommodating the x-rays machine's position indicating cylinder device in optimal configuration with the receptor in the patient's mouth.

Figure 7:
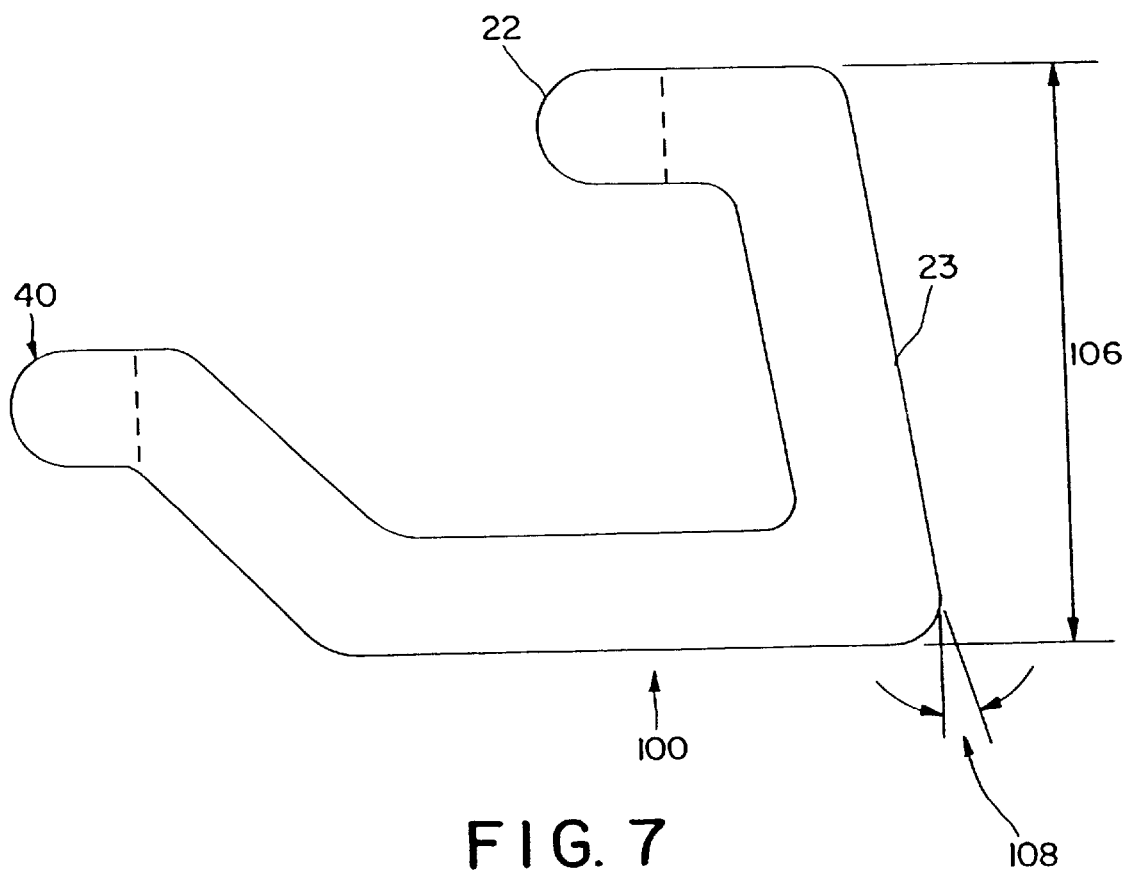
FIG. 7 is a side elevational view of another embodiment of an elongated arm of the receptor positioning device shown in FIG. 1
Figure 8:
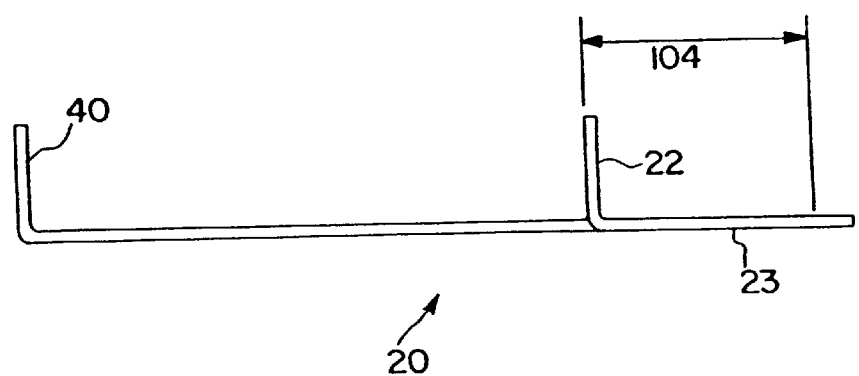
FIG. 8 is a side view of the elongated arm of FIG. 7.

Referring to FIGS. 7 and 8, another embodiment of an elongated arm 100 is shown which can be used with the receptor positioning device 10 shown in FIGS. 1–4. The elongated arm 100 includes the first end 40, the second end 22, the angled portion 21, and the short member 23 as in the embodiment shown in FIGS. 5 and 6. Again, FIG. 7 shows arm 20 as a flat blank prior to forming at the dotted lines, while FIG. 8 shows arm 20 after forming, where both ends 22 and 40 are bent approximately 90°. However, here the short member has a second length 106 which is more than the dimension 25 of the embodiment shown in FIGS. 1 and 5–6. The second length 106 is preferably about 2.85 inches. The second end 22 of the elongated arm 20, and the outer edge of the angled portion 21 define a second dimension 104 which is less than the first dimension 27 of the embodiment shown in FIGS. 1 and 5–6. The second dimension 104 is less than the first dimension shown in FIG. 5 and preferably about 1.10 inches. The outer edge of the short member 23 and the vertical plane define an angle 108 which is less than or more acute than the angle 29 of the embodiment shown in FIGS. 5 and 6 and is preferably about 7°. The more acute angle 108 better accommodates deep overbite occlusions. This other embodiment of the elongated arm has a dimension that is easily accommodated in mouths that have anatomy with deep overbites (retrognathic mandibles) ranging in size from that of a child to a large adult.

Figure 9:
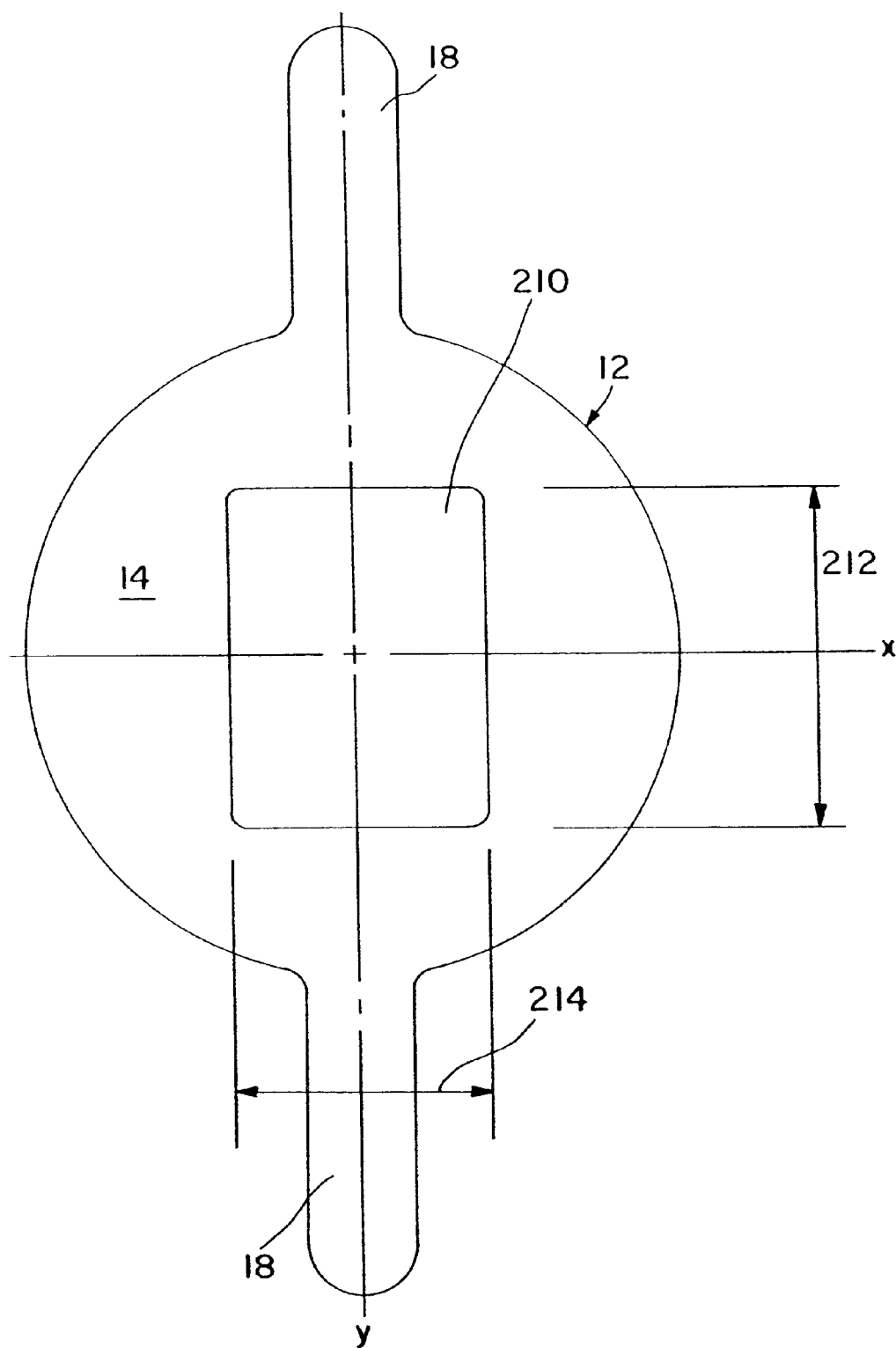
FIG. 9 is a front elevational view of another collimation plate for use with the receptor positioning device shown in FIG. 1 having a rectangular hole of different dimensions.
Figure 10:
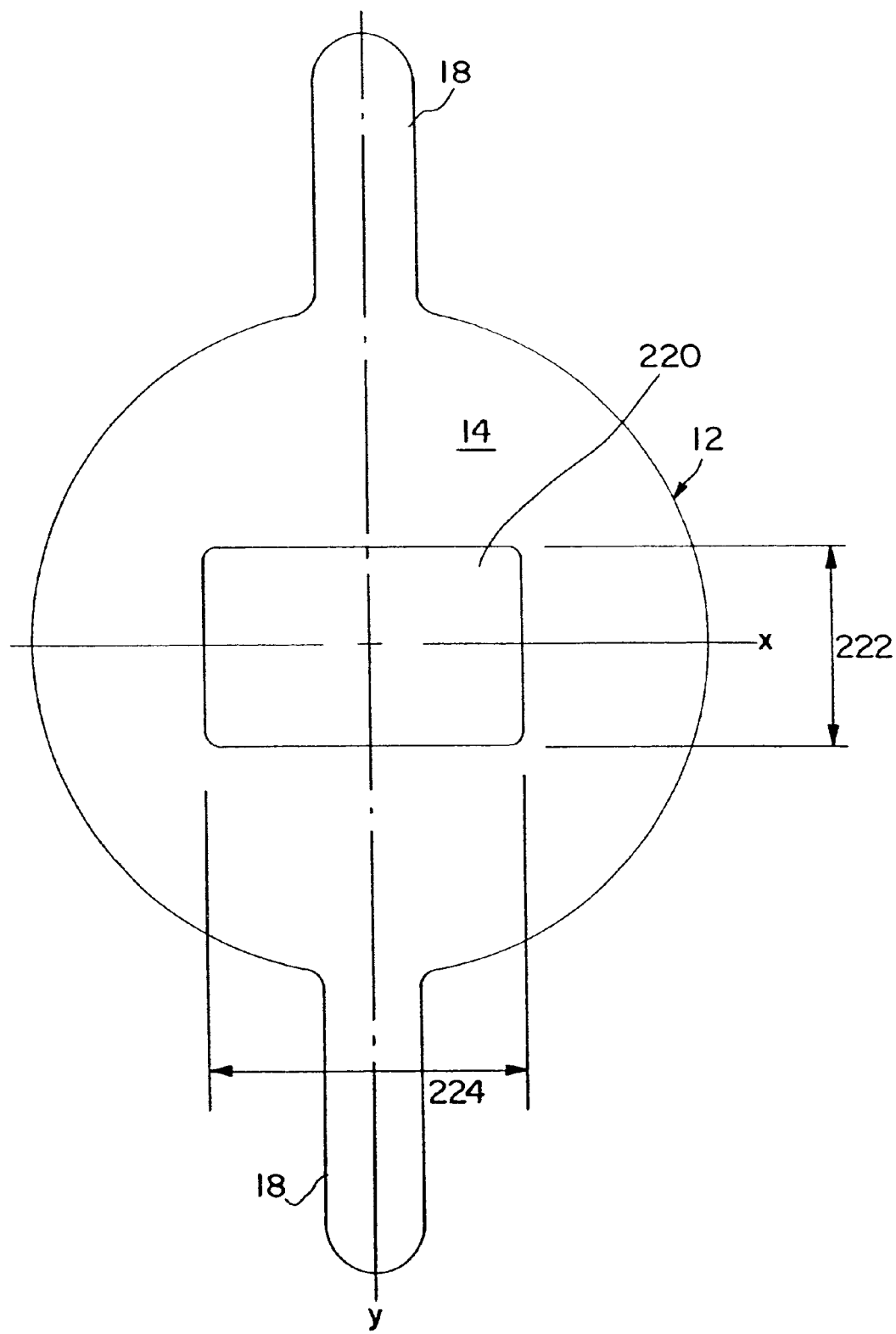
FIG. 10 is a front elevational view of another collimation plate for use with the receptor positioning device shown in FIG. 1 having a rectangular hole of still different dimensions.

Referring to FIGS. 9–10, other embodiments of a collimation plate 12 are shown including opposing elongated handles 18. Referring to FIG. 9, the collimation plate 12 further includes a preferably rectangular opening 210 positioned substantially in the center of the collimation plate 12, where the length of the opening 210 is smaller than the width. The opening 210 has a vertical dimension 212, and a horizontal dimension 214. In this embodiment, the vertical dimension 212 of the opening is preferably about 1.552 inches, and the horizontal dimension 214 is preferably about 1.210 inches. This embodiment offers a different positioning of the opening to correspond to an adult receptor or film held in the receptor holding member 28. The orientation and size of the rectangular collimation opening is for use with the adult size vertical bitewing radiographic examination. This is useful for observing compromised dentitions (with large restorations and height of alveolar crest bone decreased by marginal periodontal disease) that would not be visualized on horizontal bitewing images.

Referring to FIG. 10, the collimation plate 12 further includes a preferably rectangular opening 220 positioned substantially in the center of the collimation plate 12. The opening 220 has a vertical dimension 222, and a horizontal dimension 224. In this embodiment the vertical dimension 222 of the opening is about 1.000 inch, and the horizontal dimension 224 is preferably about 1.552 inches. This embodiment is designed to correspond to a child's receptor or film held in the receptor holding member 28. The size and orientation of the rectangular collimation opening is for use for horizontal bitewing examinations in small children (4–8 years) and very small adults or adults with limited ability to open their mouths.

Figure 12:
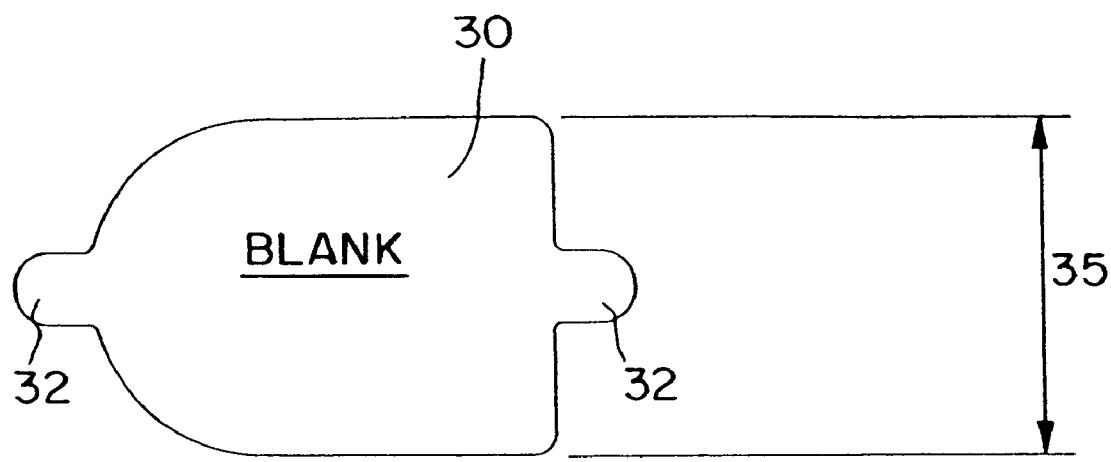
FIG. 12 is a back plate for receiving receptor of the receptor positioning device shown in FIG. 1.
Figure 13:
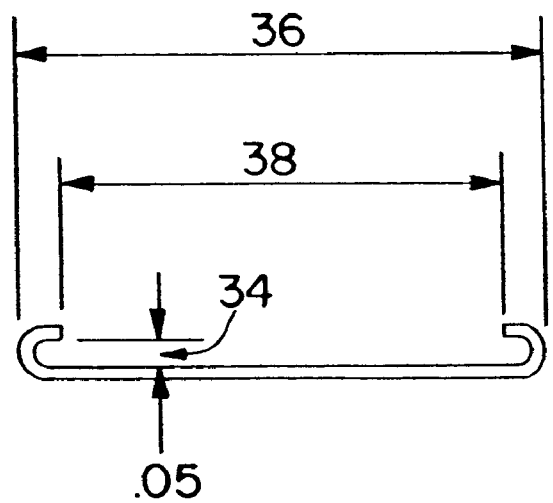
FIG. 13 is a side elevational view of the back plate of FIG. 12.

Referring to FIGS. 12 and 13, the back plate 30 is shown of the device of FIG. 1. FIG. 12 shows the flat blank for plate 30 and FIG. 13 shows plate 30 after forming. The back plate 30 includes the clips 32 and preferably has an overall length 36 of about 1.71 inches, and a dimension between the clips 38 of preferably about 1.578 inches, as they are shown formed and curled in FIG. 13. The preferred dimension 34 between the back plate 30 and the formed clip 32 is about 0.05 inches. The overall length 36 of the back plate 30 with the clips 32 curled, as shown in FIG. 13, is preferably about 1.71 inches, and the length 38 between the curled clips 32 is preferably about 1.578 inches. The width 35 of the back plate 30 is preferably about 1.20 inches. The dimensions herein accommodate standard intraoral dental film.

Figure 14:
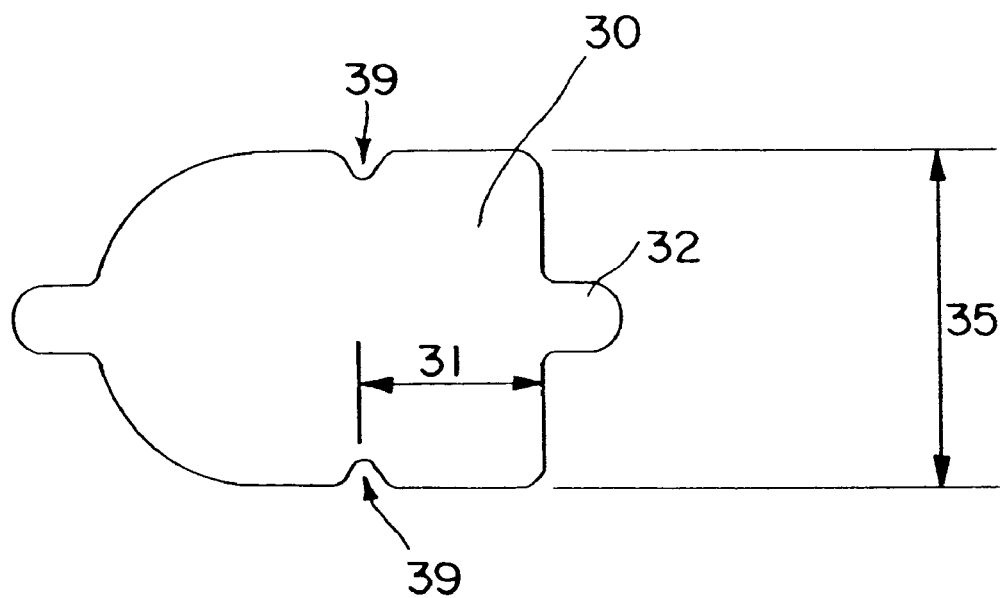
FIG. 14 is another embodiment of a back plate for receiving electronic receptors of the receptor positioning device shown in FIG. 1, having opposing notches.
Figure 15:
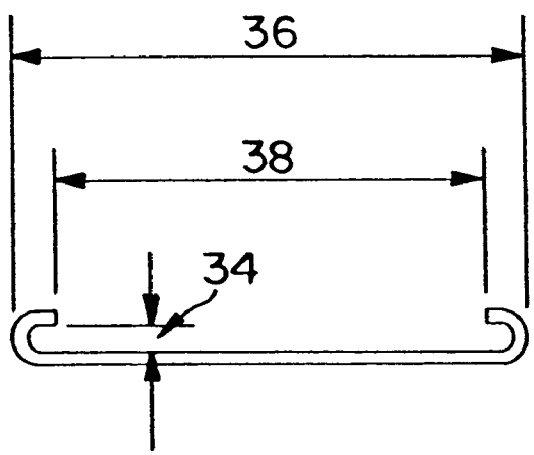
FIG. 15 is a side elevational view of the back plate of FIG. 14.

Referring to FIGS. 14 and 15, another embodiment is shown of the back plate 30. As before, FIG. 14 shows the flat blank for plate 30 and FIG. 15 shows plate 30 after forming. The embodiment shown in FIGS. 14 and 15 is the same as in the embodiment shown in FIGS. 12 and 13 except in the addition of two opposing notches 39. These notches are on opposite sides of the back plate and are on adjacent sides with reference to the clips 32. The notches 39 are a specified dimension 31 from the midpoint of the long side of the back plate 30. The dimension 31 is preferably about 0.15 inches. The notches 39 accept electronic receptors to the back plate 30 of the receptor holding member 28 with the aid of orthodontic elastics (not shown). The overall length 36, the length 38 between the curled clips 32, and the width 35 of the back plate 30 is the same as in the previous embodiment shown in FIGS. 12–13.

Other back plate sizes may be used, such as one designed for receptors or film used for children which is smaller than the films used with the back plates shown in FIGS. 12–15. Such a back plate would preferably have a length between the curled clips of about 1.60 inches long similar to the embodiments shown in FIGS. 12–15, but, a width of preferably about 1.00 inches wide to accommodate size film designed for children.

Figure 11:
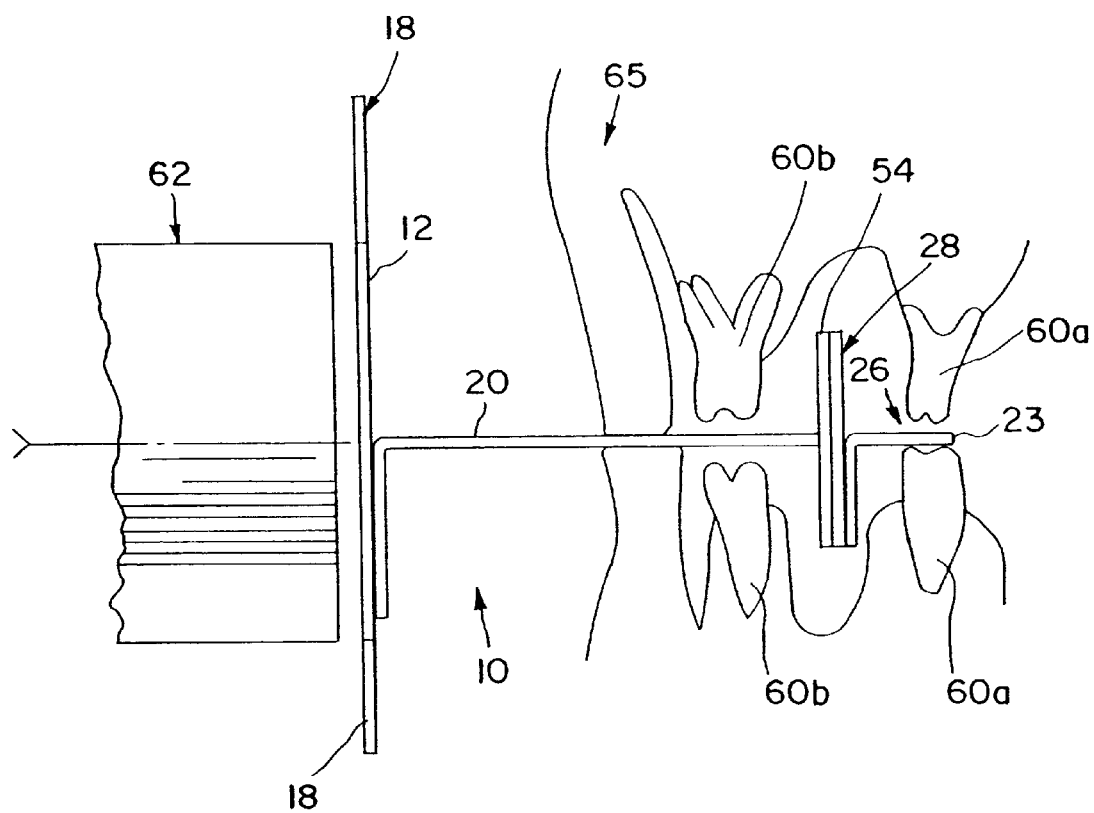
FIG. 11 is a side view of the receptor positioning device shown in FIG. 1 depicting the patient's teeth biting the device and the x-ray machine in position.

In operation and use, referring to FIG. 11, the patient's mouth 65 is outlined and the patient's teeth are above and below the elongated arm 20 of the receptor positioning device 10. Teeth 60a bite down on and grip biting portion 26 of arm 20. The receptor holding member 28 is positioned behind the teeth 60b to be exposed (on the opposite side of the mouth from teeth 60a) and the collimation plate 12 is positioned in adjacent to the patient's mouth 65 and teeth 60b. The x-ray machine 62 is positioned to take an x-ray in front of the collimation plate 12 and expose the x-ray film 54. If necessary, the patient or radiographer may use handles 18 to reposition the receptor positioning device for better comfort or aim. Preferably the collimation plate 12 is constructed of a metal and rigidly and fixedly fashioned. The rigid and fixed construction of the receptor positioning device 10 provides the most accurate film exposure because there is minimal opportunity for unwanted movement after positioning the device. The metal collimation plate having a rectangular opening 16 reduces patient exposure by absorbing approximately 50% of primary beam x-radiation for the most commonly prescribed dental radiograph, which is the bitewing. Further, the metal collimation plate reduces aiming error, that is, "cone cuts", which are frequently associated with the rectangular position-indicating device attached to the x-ray machine. Further, the use of the collimation plate of the present invention having a rectangular opening 16 reduces patient exposure to x-radiation by eliminating needless "retakes" of radiographs. The collimation plate 12 of the present invention is compatible with typical round (typically 2.75 in. diameter) indicating cylinder device that is typically standard on dental radiographic machines.

Another advantage of a device of the present invention pertains to the absorption of x-rays by the metal receptor holding member 28 which improves the quality of the acquired image on the film 54. The receptor holding member 28 is preferably constructed of a metal. The metal receptor holding member 28 will further reduce patient exposure to x-radiation by absorbing x-radiatibn that would ordinarily pass through the receptor or film 54. Also, the metal receptor holding member 28 reduces additional secondary or "scatter" radiation that causes degradation of the image.

As shown in FIGS. 1–11, the unitary design of the receptor positioning device 10 eliminates movement of multiple parts which could interfere with the exposure of the film 54. Further, the unitary design sets a fixed x-ray source to object distance and an object to film distance. Another advantage of the unitary design is the maintenance of uniform magnification and maximization of the sharpness of the acquired image. Another advantage of the receptor positioning device 10 is the preferred all metal design provides a rigid device which is also durable and lends itself to sterilizing using steam, heat or chemical methods. Moreover, the handles 18 which are part of the collimation plate 12 enables the patient to handle the device minimizing patient discomfort and malpositioning.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A receptor positioning device for taking dental bitewing radiographs of a patient's teeth, which comprises:
    a collimation plate defining a substantially central opening;
    a receptor holding member adapted to receive a receptor; and
    an elongated arm including a biting surface positioned toward a distal end thereof, the elongated arm being adapted to receive and couple at a first end to the collimation plate, the elongated arm being designed and adapted to extend towards and couple to a rear portion of the receptor holding member, opposite the collimation plate, such that an unobstructed path is defined between the substantially central opening of the collimation plate and the receptor received by the receptor holding member.

2. The device of claim 1 wherein the collimation plate, the receptor holding member, and the elongated arm are rigidly fixed together.

3. The device of claim 1 wherein the collimation plate, the receptor holding member, and the elongated arm are constructed of metal.

4. The device of claim 1 wherein the collimation plate includes handles opposite of one another for the patient to grasp.

5. The device of claim 1 wherein the opening in the collimation plate is substantially rectangular in shape and is orientated similarly to the film having a substantially rectangular shape.

6. The device of claim 1 wherein the substantially central opening defined by the collimation plate is adapted to correspond dimensionally to the dimensions of the receptor.

7. The device of claim 1 wherein the biting surface is adjacent to the receptor holding member such that the receptor is positioned behind the patient's teeth.

8. The device of claim 1 wherein the receptor holding member accommodates a plurality of receptor dimensions.

9. The device of claim 1 wherein the receptor holding member accommodates a digital receptor.

10. The device of claim 1 wherein the receptor holding member accommodates a film.

11. A receptor positioning device for taking dental bitewing radiographs of teeth inside a patient's mouth, which comprises:

a rigid, fixed structure including
- a collimation plate defining a substantially rectangular opening;
- a receptor holding member adapted to receive a receptor;
- an elongated arm being adapted to receive and couple at a first end to the collimation plate, the elongated arm being designed and adapted to extend towards and couple at a second end to a rear portion of the receptor holding member, opposite the collimation plate, such that an unobstructed path is defined between the substantially rectangular opening of the collimation plate and the receptor received by the receptor holding member; and
- a biting surface fixedly attached to a distal end of the elongated arm and adjacent to the receptor holding member such that the receptor is positioned behind the teeth on which the radiographs are being taken while the biting surface is gripped by teeth on the opposite side of the patient's mouth.

12. A method for taking dental bitewing radiographs of a patients' teeth comprising:

providing a rigid fixed structure including a collimation plate defining a substantially central opening, a receptor holding member adapted to receive a receptor, an elongated arm being adapted to receive and couple at a first end to the collimation plate, the elongated arm being designed and adapted to extend towards and couple to a rear portion of the receptor holding member such that an unobstructed path is defined between the substantially rectangular opening of the collimation plate and the receptor received by the receptor holding member;

providing a biting surface being fixedly attached to a distal end of the elongated arm and adjacent to the receptor holding member such that the receptor is positioned behind the patient's teeth on which the radiographs being taken while the biting surface is gripped by teeth on the opposite side of the patient's mouth;

positioning the patient's teeth for biting on the biting surface such that an unobstructed path is defined between the collimation plate and the receptor received by the receptor holding member;

aligning an x-ray machine with the opening of the collimation plate; and exposing the receptor such that x-radiation from the x-ray machine passes along the unobstructed path defined between the collimation plate and the receptor.

* * * * *